United States Patent [19]
Kawai et al.

[11] Patent Number: 5,045,068
[45] Date of Patent: Sep. 3, 1991

[54] FLOW RATE REGULATOR FOR LIQUID MEDICINE OR BLOOD TRANSFUSION UNIT

[75] Inventors: Tatsuya Kawai; Takashi Matsuda, both of Hiroshima, Japan

[73] Assignee: Japan Medical Supply Company Limited, Hiroshima, Japan

[21] Appl. No.: 335,408

[22] Filed: Apr. 10, 1989

[51] Int. Cl.$^5$ .............................................. A61M 5/00
[52] U.S. Cl. .................... 604/246; 604/248; 604/32; 251/200; 251/352
[58] Field of Search ............. 604/246, 247, 248, 251, 604/118, 122, 32; 251/200, 352

[56] References Cited

U.S. PATENT DOCUMENTS

| | | | |
|---|---|---|---|
| 3,323,774 | 6/1967 | Wilson | 251/352 |
| 4,300,250 | 4/1983 | Stoll | 251/208 |
| 4,428,397 | 1/1984 | Bron | 137/504 |
| 4,544,130 | 10/1985 | Stoll et al. | 251/200 |
| 4,738,665 | 4/1988 | Shepard | 604/248 |
| 4,769,012 | 9/1988 | Quang et al. | 604/247 |
| 4,802,506 | 2/1989 | Aslanian | 604/246 |

Primary Examiner—C. Fred Rosenbaum
Assistant Examiner—Kathleen A. Daley
Attorney, Agent, or Firm—Cushman, Darby & Cushman

[57] ABSTRACT

A flow rate regulator includes a first cylindrical member, a second cylindrical member and a disc-shaped member to regulate, the flow rate of liquid flowing through a transfusion unit. The liquid is introduced into the second cylindrical member via an inlet port. It flows through the disc-shaped member via a through hole and flows further along a peripherally extending groove in the first cylindrical member. Then, it is discharged from the first cylindrical member via an outlet port after the flow rate is regulated as required. The disc-shaped member is fitted in the second cylindrical member so as not to be rotated relative to the latter, and the sub-assembly is then fitted into the first cylindrical member. The peripherally extending groove is so designed that its cross-sectional area is gradually varied on the bottom portion of the first cylindrical member. The through hole in the disc-shaped member is communicated with the peripherally extending groove. A position where the through hole in the disc-shaped member is communicated with the peripherally extending groove in the first cylindrical member is varied by rotating the first cylindrical member so that a cross-sectional area of the peripherally extending groove is varied correspondingly. This allows the flow rate of the liquid flowing through the regulator to be adjusted as required.

5 Claims, 2 Drawing Sheets

FLOW RATE REGULATOR FOR LIQUID MEDICINE OR BLOOD TRANSFUSION UNIT

BACKGROUND OF THE INVENTION

1. Field of the Invention

The present invention relates to a flow rate regulator used for a liquid or blood transfusion unit to regulate a flow rate of liquid medicine or blood flowing therethrough. Further, the present invention relates to a liquid medicine or blood transfusion unit having the flow rate regulator used therefor.

2. Description of the Related Art

When a medical instrument such as a liquid medicine applicator, a blood transfusion unit or the like is used, it is necessary to regulate the flow rate of the liquid medicine or blood flowing through a tube. To this end, it is well known that a flow rate regulating device is disposed midway of the tube.

Many kinds of flow rate regulating devices have been heretofore known. Among the many conventional simple and inexpensive flow rate regulating devices, a typical one is designed in the form of a roller clamp. The roller clamp is constructed by a housing and a roller rotatably accommodated in the housing. A tube through which liquid medicine or blood flows is clamped between the housing having a suitable angle of inclination and the outer peripheral surface of the roller. Accordingly, the flow rate of the liquid medicine or blood is regulated, as required, by properly varying the degree of clamping by displacing the roller toward or away from the housing.

With the above described roller clamp, it has been found that the throat portion of a tube is deformed as time elapses, causing the flow rate to be reduced gradually due to gradual reduction of the effective cross-sectional area of the tube. To obviate the foregoing problem, several improvements have been tried. One of the improvements which has been put in practical use, involves a roller clamp including a housing having a bottom which is formed with V-shaped grooves. However, this improved roller clamp suffers from the problem that the flow rate varies under the influence of temperature variations, although variation of the flow rate over time has been reduced remarkably when the improved roller clamp is used at a constant temperature.

In addition to the aforementioned roller clamps conventional flow rate regulating devices are disclosed in, for example, U.S. Pat. Nos. 3,877,428, 4,428,397 and 4,769,012 and Japanese Laid-Open Patent No. 247,470/1986. Each one of the conventional flow rate regulating devices is constructed by combining and assembling a plurality of components together so as to allow the flow rate to be regulated by varying the cross-sectional area of the flowing passage. The respective flow rate regulating devices disclosed in the prior U.S. patents have drawbacks in that they are complicated in structure and require a plurality of split molding dies for molding the components, resulting in high manufacturing cost, particularly driven by increased expenditure required for the molding dies. On the other hand, the conventional flow rate regulating device disclosed in the Japanese laid open patent is constructed merely by two components. However, it has been found that this flow rate regulating device also has drawbacks in that it has a narrow range of flow rate regulation and it has a low flow rate accuracy. Accordingly, it can be concluded that all of the conventional flow rate regulating devices have limited practicability.

SUMMARY OF THE INVENTION

The present invention has been made with the foregoing background in mind and one object of the invention resides in providing a flow rate regulator usable for a liquid medicine applicator or blood transfusion unit which is entirely free from the drawbacks inherent in the conventional flow rate regulating devices Accordingly, the present invention assures that the flow rate is hardly varied over time, and that the flow rate hardly varies as the environmental temperature fluctuates.

Another object of the present invention is to provide a flow rate regulator usable for a liquid medicine applicator or blood transfusion unit which assures that the flow rate can be regulated at high accuracy, during liquid medicine or blood transfusion.

Another object of the present invention is to provide a flow rate regulator usable for a liquid medicine applicator or blood transfusion unit which is simple in structure and which can be easily manufactured at low cost.

To accomplish the above objects, the present invention provides a flow rate regulator usable for a liquid medicine applicator or blood transfusion unit having a first cylindrical member including a bottom portion. The first cylindrical member is formed with a peripherally extending groove on its bottom portion, The cross-sectional area of which is varied gradually. The peripherally extending groove is communicated with an outlet port via a through hole in the first cylindrical member. A second cylindrical member, including a bottom portion to be rotatably fitted in the first cylindrical member, is also provided. The second cylindrical member has a through hole formed therein which communicates with an inlet port. A disc-shaped member is adapted to be fitted in the second cylindrical member so as not to be rotated relative to the latter. The disc-shaped member is brought in close contact with the bottom portion of the first cylindrical member and has a through hole formed therein which is communicated with the peripherally extending groove on the bottom portion of the first cylindrical member, as well as with the through hole in the second cylindrical member.

According to a preferred embodiment of the present invention, a radially extending groove is formed on the bottom portion of the first cylindrical member and connects with the peripherally extending groove on the bottom portion of the first cylindrical member. The radially extending groove, in turn, communicates with the through hole in the first cylindrical member so that an inlet port on the second cylindrical member is located in axial alignment with an outlet port on the first cylindrical member.

In the case where it is not necessary that the inlet port on the second cylindrical member and the outlet port on the first cylindrical member are arranged along the central axis of the flow rate regulator, the radially extending communication groove on the first cylindrical member and the radially extending communication groove on the disc-shaped member are not required any longer.

The peripherally extending groove in the first cylindrical member has an interrupted part so that flowing of the liquid medicine or blood through the regulator is interrupted as long as the through hole in the disc-shaped member is located within the range of the interrupted part.

The first cylindrical member, the second cylindrical member and the disc-shaped member are molded of plastic material, respectively. To assure that the disc-shaped member is normally brought in close contact with the bottom portion of the first cylindrical member, it is preferable that the disc-shaped member is molded of plastic material having higher elasticity than that of plastic material employed for the first cylindrical member and the second cylindrical member.

Further, the present invention provides a liquid medicine applicator or blood transfusion unit having the aforementioned flow rate regulator used therefor.

To remove fine foreign materials in the liquid medicine or blood, it is preferable that a filter is disposed upstream of the flow rate regulator.

These and other objects, features and advantages of the present invention will be readily apparent from the following description and with reference to the accompanying drawings.

BRIEF DESCRIPTION OF THE DRAWINGS

The present invention will be illustrated in the following drawings in which.

DESCRIPTION OF THE PREFERRED EMBODIMENT

Now, the present invention will be described in greater detail hereinafter with reference to the accompanying drawings which illustrate a preferred embodiment thereof.

Figure 1:
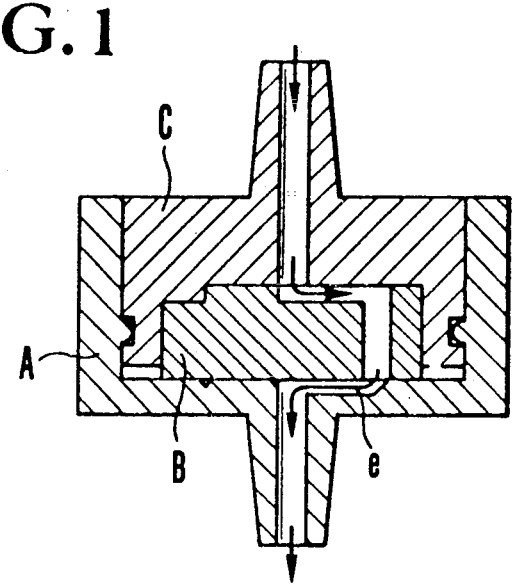
FIG. 1 is a sectional view taken along the axis line of a flow rate regulator in accordance with an embodiment of the present invention.
Figure 3:
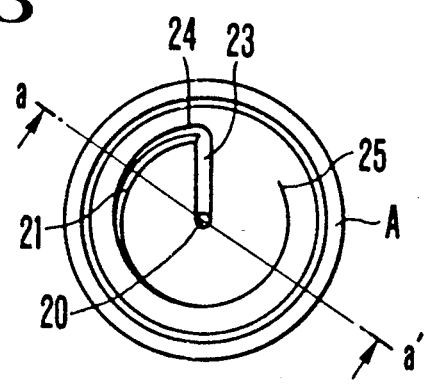
FIG. 3 is a plan view of a first cylindrical member constituting the flowing rate regulator of the present invention.
Figure 4:
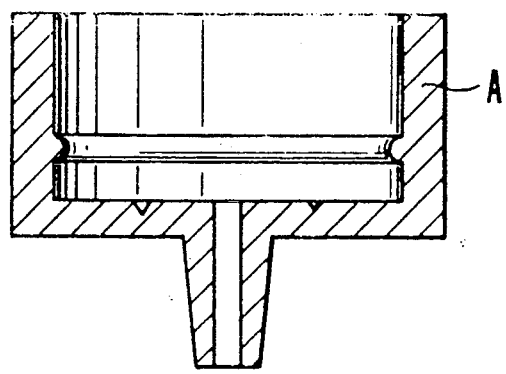
FIG. 4 is a sectional view of the first cylindrical member taken along line a—a' in FIG. 3.

A flow rate regulator in accordance with the present invention is substantially constituted by a first cylindrical member A, a disc-shaped member B and a second cylindrical member C. Specifically, the first cylindrical member A has a bottom portion 19 which is formed with a peripherally extending groove 21 having a V-shaped contour in cross section. As is best seen in FIG. 3, the groove 21 has a width and a depth which gradually increases from a start point 25 to an end point 24. With this construction, the groove 21 has a cross-sectional area which increases gradually. The groove 21 communicates with a radially extending groove 23 on the bottom portion 19 via the end point 24 having the largest cross-sectional area. The groove 23 has more than or the same cross-sectional area as that of the groove 21. As is apparent from the drawing, the groove 23 extends toward the center of the bottom portion 19 until it is communicated with a through hole 20 in the first cylindrical member A.

The disc-shaped member B has also a through hole 18 formed therein which is communicated with the groove 21 when the disc-shaped member B is assembled in the first cylindrical member A. With such construction, liquid medicine or blood to be transfused (hereinafter referred to simply as liquid) is first caused to flow in the narrow part of the groove 21 via the through hole 18 in the disc-shaped member B and thereafter it flows further therefrom to the wide part of the groove 21. Accordingly, the start point 25 of the groove 21 when communicated with the through hole 18 in the disc-shaped member B defines the smallest cross-sectional area along the whole flow passage of the liquid, so that the smallest flow rate is determined by the start point 25 of the groove 21. As the through hole 18 comes near to the end point 24 of the groove 21 by rotating the first cylindrical member A with an operator's hand, the flow rate is increased more and more. On the contrary, as the through hole 18 comes near to the start point 25, the flow rate is reduced more and more. In this connection, it should be noted that flowing of the liquid is interrupted as long as the through hole 18 is located at a region on the bottom portion 19 where no groove is formed in the first cylindrical member A, as is best seen in FIG. 3.

Figure 2:
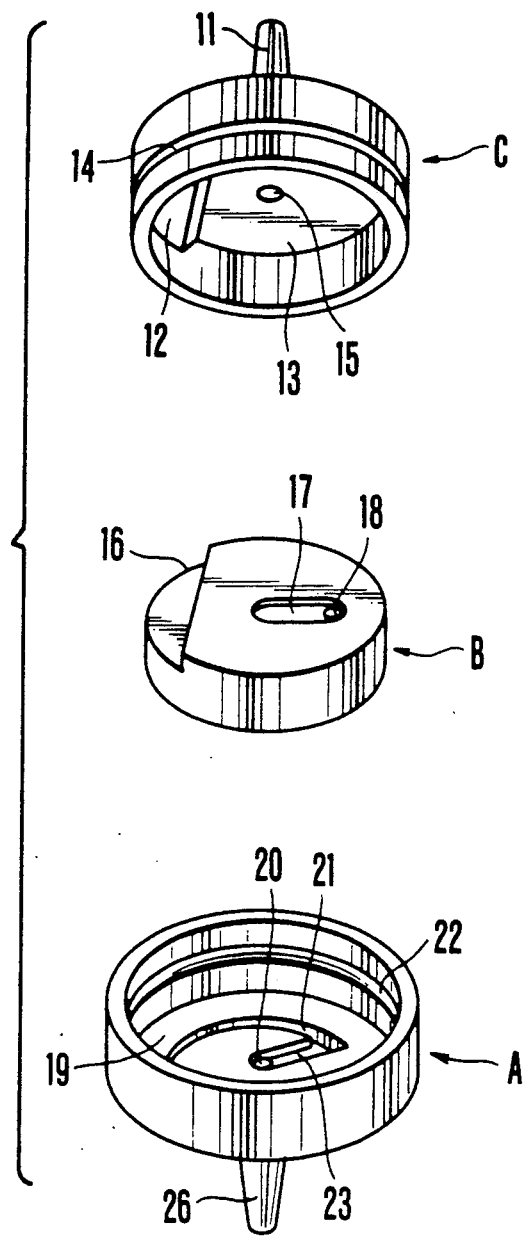
FIG. 2 is a perspective view of the flowing rate regulator in FIG. 1, shown in a disassembled state.

The disc-shaped member B is formed with a radially extending groove 17 on the upper surface thereof which extends from the through hole 18 to the center of the second cylindrical member B. In addition, as is apparent from FIG. 2, the disc-shaped member B is formed with a cutout 16 on the upper surface.

The second cylindrical member C has a through hole 15 formed at the center of a bottom portion 13, and a protrusion 12 is provided inside of the second cylindrical member C at a position corresponding to the cutout 16 on the disc-shaped member B.

The protrusion 12 on the second cylindrical member C and the cutout 16 on the disc-shaped member B are provided to assure that member B and the member C are not rotated relative to each other. It should of course be understood that the present invention should not be limited only to the foregoing provision for the purpose of inhibiting the members B and C from being rotated relative to each other. As will be evident to these skilled in the art other relative rotation inhibiting means may be employed for the same purpose.

The three members A, B and C, as constructed in the above-described manner, are assembled together in such a manner that the member B is first fitted inside of the member C and the sub-assembly is then fitted inside of the member A. In the illustrated embodiment, the member A is provided with an annular protrusion 22 around its inner wall surface and the member C is formed with an annular groove 14 around the outer wall surface so that both the members A and C are rotatably assembled together by fitting the protrusion 22 in the groove 14. Moreover, the positional relationship of the annular protrusion 22 relative to the annular groove 14 should be set so that the member B is brought in close contact with the bottom surface of the member A in the presence of the member C. To this end, it is preferable that elastomeric material such as plasticizable polyvinyl chloride, polyurethane, silicone rubber or the like is employed for the member B rather than hard plastic material.

Next, operations of the flow rate regulator as constructed in the aforementioned manner will be described below.

A liquid is introduced into the interior of the member C via an inlet port 11 and the through hole 15. It flows through the groove 17 and the through hole 18 in the member B and further flows through the grooves 21 and 23 on the member A until it is discharged from an outlet port 26. Regulating of a flow rate is achieved by rotating the member C relative to the member A and vice versa. As the member C is rotated along with the member B, the positional relationship of the through hole 18 in the member B relative to the groove 21, on the bottom portion of the member A, is varied so that the cross-sectional area of the groove 21 is varied correspondingly. This makes it possible to regulate the flow rate to a required value. If both the members A and C are calibrated in a suitable manner, calibrations prepared on them can be used as a measure for setting a flow rate as required.

In the foregoing embodiment, both the grooves 17 and 23 are formed in order to assure that the inlet port 11 and the outlet port 26 are located along the axis line of the flow rate regulator of the present invention. However, if the inlet port 11 and the through hole 15 in the member C are located in alignment with the through hole 18 in the member B and the outlet port 26 and the through hole 20 in the member A are located in alignment with the start point 25 of the groove 23, then grooves 17 and 23 will not be required. It should be noted that a manner of fitting the member A onto the member C should not be limited only to the aforementioned arrangement. As will be evident to those skilled in the art other arrangements may be employed.

Generally, either a liquid medicine transfusion unit or blood transfusion unit is constituted by a bottle needle, a drip chamber, a vein needle and a tube connected to the latter. Preferably, the flow rate regulator of the present invention is incorporated in the upper part or the lower part of the drip chamber. The regulator may be united with the drip chamber. Alternatively, the regulator may be disposed midway of a liquid medicine or blood transfusion line. Since the flow rate is varied when the flow rate regulating part of the regulator is clogged with some foreign material, it is preferable that a filter is disposed upstream of the regulator. Particularly, in the case of the liquid medicine transfusion unit, it is essential that a filter is provided for the unit, because there is a danger that fine particles are introduced into liquid medicine after the bottle needle is penetrated through a rubber cap on the bottle and thereby a part of the rubber cap is cut off. To prevent any foreign material from being introduced into the body of a patient, a filter is often incorporated in the liquid medicine or blood transfusion unit. Provision of the filter in that way makes it possible to reduce the number of components for the transfusion unit. It is preferable that pores in the filter have a diameter in the range of 0.1 to 30 microns.

To facilitate understanding of properties of the flow rate regulator in accordance with the present invention, an additional description will be made in accordance with results derived from tests conducted using the regulator.

The members A and C were molded of ABS resin and the member B was molded of plasticizable polyvinyl chloride. These members were assembled together in the above-mentioned manner to provide a flow rate regulator. The regulator was incorporated in a liquid medicine transfusion unit. To what degree the flow rate varied as time elapsed was observed while water having a temperature varying from 5° to 40° C. was caused to flow through the transfusion unit under a differential height of 65 cm. For the purpose of making a comparison, similar tests were conducted using a roller clamp which was of the type having a reduced amount of fluctuation in the flow rate. The roller clamp used for the tests included a roller which had a V-shaped groove formed thereon. Results derived from the tests are as shown in Table 1.

TABLE 1

| | flow rate in milliliter per minute environmental temperature | | | |
|---|---|---|---|---|
| | 20.5° C. | 5.8° C. | 39.0° | 9.8° C. |
| present invention | 44.8 | 34.2 | 49.2 | 30.8 |
| compared example | 40.6 | 24.0 | 151.8 | 68.2 |

As will be readily apparent from Table 1, the flow rate regulator of the present invention exhibits relatively small fluctuation in the flow rate with variation of the environmental temperature. In contrast with the regulator of the present invention, the conventional clamp roller exhibits a relatively large amount of fluctuation in the flow rate with variation of the environmental temperature. It will be readily understood that the flow rate can be maintained in a very stable state by disposing a filter upstream of the flow rate regulator.

While the present invention has been described above with respect to a preferred embodiment thereof, it should of course be understood that it should not be limited only to the preferred embodiment, but that various changes or modifications may be made without departure from the scope of the present invention as defined by the appended claims.

What is claimed is:

1. A flow rate regulator usable for a liquid medicine or blood transfusion unit comprising:

a first cylindrical member including upper and lower ends, a bottom portion which substantially closes off the lower end, an outlet port which extends outwardly from said bottom portion, and a peripherally extending groove on said bottom portion, the cross-sectional area of said peripherally extending groove continually and gradually varying, said first cylindrical member further including a radial groove and a through hole in said bottom portion for connecting the peripherally extending groove with said outlet port via said through hole and said radial groove, and an annular protrusion formed on the inner cylindrical surface at the location between said upper and lower ends;

a second cylindrical member having upper and lower ends and including a bottom portion which substantially closes off the upper end, said second cylindrical member being rotatably fitted in the first cylindrical member and having a projection extending from said bottom portion, said second cylindrical member further including a through hole in said bottom portion, an inlet port which extends outwardly from said bottom portion and which communicates with said through hole in said bottom portion, and an annular groove formed on the outer cylindrical surface at a location between said upper and lower ends;

a disc-shaped member having a cut out portion which mates with said projection of said second cylindrical member so that said disc-shaped member will not be rotated relative to said second cylindrical member when fitted therein, said disc-shaped member being brought in close contact with said bottom portion of said first cylindrical member and having a through hole and a radial groove formed therein for connecting said peripherally extending groove on said bottom portion of said first cylindrical member with said through hole in said second cylindrical member when said first and second cylindrical members are rotatably fitted together with said disc-shaped member therebetween, by causing said annular protrusion of said first cylindrical member to enter said annular groove of said second cylindrical member.

2. The flow rate regulator as claimed in claim 1 wherein said peripherally extending groove extends less than 360° in said first cylindrical member, which prevents a liquid from flowing therethrough as long as said through hole in said disc-shaped member is rotated away from said peripherally extending groove.

3. The flow rate regulator as claimed in claim 1, wherein the first cylindrical member, the second cylindrical member and the disc-shaped member are molded of plastic material, respectively, and the disc-shaped member is molded of plastic material of which elasticity is determined higher than that of plastic material used for molding the first cylindrical member and the second cylindrical member so that the disc-shaped member is brought in close contact with the bottom portion of the first cylindrical member.

4. A liquid medicine or blood transfusion unit using the flow rate regulator as defined in claim 1, wherein the flow rate regulator is incorporated in said transfusion unit.

5. A liquid medicine or blood transfusion unit using the flow rate regulator as defined in claim 1, wherein a filter is disposed upstream of the flow rate regulator.

* * * * *